US005480966A

United States Patent [19]
Sommé et al.

[11] Patent Number: 5,480,966
[45] Date of Patent: Jan. 2, 1996

[54] PEPTIDES DERIVED FROM THE ENVELOPE GLYCOPROTEIN OF HIV VIRUSES, THEIR APPLICATIONS TO THE DETECTION OF INFECTION CAUSED BY THESE VIRUSES AND TO THE VACCINATION AGAINST AIDS

[75] Inventors: Gérard Sommé, Gif-Sur-Yvette; Jacques Martin, Paris, both of France

[73] Assignee: Clonatec, S.A., Paris Cedex, France

[21] Appl. No.: 116,252

[22] Filed: Sep. 2, 1993

Related U.S. Application Data

[63] Continuation of Ser. No. 641,455, Jan. 14, 1991, abandoned.

[30] Foreign Application Priority Data

Jan. 16, 1990 [FR] France .................... 90 00455
Jan. 16, 1990 [FR] France .................... 90 00456

[51] Int. Cl.$^6$ .................. C07K 14/155; C07K 17/00; A61K 39/24; G01N 33/536
[52] U.S. Cl. .................. 530/324; 530/326; 530/806; 424/188.1; 424/196.11; 424/202.1; 435/7.1; 435/975
[58] Field of Search .................. 530/324, 326, 530/806, 826, 388.35, 389.4, 403; 424/188.1, 196.11, 202.1, 208.1; 435/7.1, 975

[56] References Cited

U.S. PATENT DOCUMENTS

| | | | |
|---|---|---|---|
| 4,499,080 | 2/1985 | Duflot et al. | 514/12 |
| 4,629,783 | 12/1986 | Cosand | 530/324 |
| 4,735,896 | 4/1988 | Wang et al. | 530/324 |
| 4,768,607 | 9/1988 | Molina | 180/165 |
| 4,812,556 | 3/1989 | Vahlne et al. | 530/324 |
| 4,879,212 | 11/1989 | Wang et al. | 530/324 |
| 4,957,737 | 9/1990 | Heimer et al. | 530/324 |
| 5,128,319 | 7/1992 | Arlinghaus | 514/13 |
| 5,260,189 | 11/1993 | Formoso et al. | 530/326 |
| 5,283,320 | 2/1994 | Vahlne et al. | 530/325 |
| 5,338,829 | 8/1994 | Weiner et al. | 530/324 |

FOREIGN PATENT DOCUMENTS

| | | |
|---|---|---|
| 0214709 | 3/1987 | European Pat. Off. |
| 0247557 | 12/1987 | European Pat. Off. |
| 0251612 | 1/1988 | European Pat. Off. |
| 0278148 | 8/1988 | European Pat. Off. |
| 0284383 | 9/1988 | European Pat. Off. |
| 0292454 | 11/1988 | European Pat. Off. |
| 0326490 | 8/1989 | European Pat. Off. |
| 0388602 | 9/1990 | European Pat. Off. |
| 8805440 | 7/1988 | WIPO |
| WO8903844 | 5/1989 | WIPO |
| 9015071 | 12/1990 | WIPO |

OTHER PUBLICATIONS

Klasse et al., "Presence of antibodies to a putatively immunosuppressive part of human immunodeficiency virus (HIV) envelope glycoprotein gp41 is strongly associated with health among HIV–positive subjects" P.N.A.S. USA 85:5225–6229 (Jul. 1988).

Guyader, et al., "Genome organization and transactivation of the human immunodeficiency virus type 2.", Nature 326:662–669 (Apr. 1987).

Schulz et al, *Principles of Protein Structure*, pp. 14–16, Springer–Verlag (NY) 1979.

Robinson et al, "Antibodies to the Primary Immunodominant Domain of Human Immunodeficiency Virus Type 1 (HIV–1) Glycoprotein gp 41 . . . " *J. Virol.* 64(11):5301–5305 (Nov. 1990).

Hunt et al, "Discrimination Between HIV–1 and HIV–2 . . . " *AIDS Res. Hum. Retrovir.* 6(7):883–898 (Jul. 1990).

Goodman–Snitkoff et al, "Defining Minimal Requirements for Antibody Production . . . " *Vaccine* 8(3): 257–262 (Jun. 1990).

Schulz and Schirmer, *Principles of Protein Structure*, pp. 14–16, 1979.

*Primary Examiner*—Stephen G. Walsh
*Attorney, Agent, or Firm*—Ratner & Prestia

[57] ABSTRACT

Peptides are derived from the envelope glycoprotein of HIV virus and having one of the following formulae (Seq. ID NO: 1)               (I)
X—Arg—Ile—Leu—Ala—Val—Glu—Arg—Tyr—Leu—Lys—Asp—Gln—Gln—Leu—Leu—Cly—Ile—Trp—Gly—Cys—Ser—Gly—Lys—Leu—Ile—Cys—Z (Seq. ID NO: 2)               (II)
X—Ala—Ile—Glu—Lys—Tyr—Leu—Gln—Asp—Gln—Ala—Arg—Leu—Asn—Ser—Trp—Gly—Cys—Ala—Phe—Arg—Gln—Val—Cys—Z in which X represents an NH$_2$ group which is free or converted into an amide by one or two alkyl groups comprising from 1 to 5 carbon atoms, and Z represents either an OH group which is free or present as an alkoxy and thereby containing an alkyl group comprising from 1 to 5 carbon atoms, and in which at least one of the Cys residues is deleted, substituted or protected.

The peptides are applied to the detection of infection caused by the viruses HIV-1 and/or HIV-2 and to the vaccination against AIDS.

12 Claims, No Drawings

PEPTIDES DERIVED FROM THE ENVELOPE GLYCOPROTEIN OF HIV VIRUSES, THEIR APPLICATIONS TO THE DETECTION OF INFECTION CAUSED BY THESE VIRUSES AND TO THE VACCINATION AGAINST AIDS

This application is a continuation of U.S. application Ser. No. 07/641,455 filed on Jan. 14,1991, by the same inventors, now abandoned.

BACKGROUND OF THE INVENTION

1. Field of the Invention

The present invention relates to antigenic peptides which are capable of being recognised by the antibodies induced in man by retroviruses of the type HIV in accordance with the nomenclature defined in the journal Nature. The invention also relates to peptides which possess immunogenic properties or which are capable of being made immunogenic in vivo. The invention furthermore relates to applications of these peptides to the preparation of a composition for the in vitro diagnosis of AIDS in man and to the production of immunogenic compositions and vaccine compositions against the HIV viruses.

Similarly, the invention relates to the applications, with a view to the same objectives, of antibodies capable of being induced in vivo by immunogenic peptides or peptides made immunogenic, and their applications to the production of the active ingredients of drugs against certain forms of AIDS.

The invention also relates to the use of these peptides in processes for the in vitro diagnosis of infection by the viruses HIV-1 and/or HIV2, as well as the reagents or diagnostic kits for carrying out the said processes.

2. Description of the Background

A first retrovirus, named HIV-1, has been described in European Patent Application No. 138 667 of Sep. 14, 1984. A second retrovirus, named HIV-2, has been described in European Patent Application No. 239 425 of Jan. 22, 1987. These two retroviruses preferably have as their target human T4 lymphocytes and exhibit a cytopathogenic effect toward these lymphocytes.

Lysates of the HIV-1 viruses contain nuclear proteins called proteins gag and pol, which exhibit 60% homology with the corresponding gag and pol proteins of the HIV-2 viruses, and envelope proteins called env proteins which exhibit only 40% homology with the corresponding env proteins of the HIV-2 viruses.

These lysates have been used in diagnostic tests for AIDS. In order to increase the specificity of these tests, it has been proposed to substitute for the virus lysates products which do not originate from cells infected by the virus, such as synthetic peptides or peptides obtained from recombinant organisms.

Studies carried out on the different proteins of the viruses HIV-1 and HIV-2 have made it possible to distinguish peptides having identical or similar sequences to the sequences obtained in the gag proteins or in the env proteins of these viruses. Such peptides, obtained from the predominant proteins of the virus HIV-1, have been described, especially in U.S. Pat. No. 4,629,783. Peptides obtained from the predominant proteins of the virus HIV-2 have been described, especially in French Patent Application No. 2 610 632.

Peptides obtained from the gp41 and gp42 glycoproteins of the viruses HIV-1 and HIV-2, modified at their ends in order to facilitate the coupling of the said peptides to supports or carrier molecules, have likewise been proposed for diagnostic or therapeutic purposes.

Peptides made cyclic through the formation of disulphide bridges between two cysteine residues have also been proposed in European Patent Application No. 326 490.

SUMMARY OF THE INVENTION

This invention relates to a peptide having a formula selected from the group consisting of (Seq. ID NO: 1)      (I)
X—Arg—Ile—Leu—Ala—Val—Glu—Arg—Tyr—Leu—Lys—Asp—Gln—Gln—Leu—Leu—Gly—Ile—Trp—Gly—Cys—Ser—Gly—Lys—Leu—Ile—Cys—Z;

and (Seq. ID NO: 2)      (II)
X—Ala—Ile—Glu—Lys—Tyr—Leu—Gln—Asp—Gln—Ala—Arg—Leu—Asn—Ser—Trp—Gly—Cys—Ala—Phe—Arg—Gln—Val—Cys—Z wherein X represents $NR_2$, where R is selected from the group consisting of H and $(C_1-C_5)$alkyl;

Z represents OR, wherein R is selected from the group consisting of hydrogen and $(C_1-C_5)$alkyl;

at least one of the Cys residues is deleted, substituted, or protected;

the bonds between amino acids in the peptide are selected from the group consisting of —CO—NH—, —CO—N(CH$_3$)—, —CH$_2$—CH$_2$— and —CO—CH$_2$— bonds; and the peptide has a backbone that may comprise in addition to the above amino acids at least one residue selected from the group consisting of —CH$_2$—, —NH— and —O—;

fragments thereof; and oligomers thereof.

This invention also relates to an immunogenic composition, that comprises at least one of the peptides of the invention, a conjugate thereof with a carrier or a mixture thereof; and a pharmaceutically-acceptable vehicle for the production of a vaccine, wherein the composition is capable of inducing the production of anti-peptide antibodies, the peptide, conjugate thereof or mixture thereof being present in an amount effective to inhibit a retrovirus selected from the group consisting of the HIV-I and HIV-II retroviruses.

Also provided herein an in vitro method of diagnosing infection by a retrovirus selected from the group consisting of HIV-I and HIV-II in a biological sample, comprising contacting a biological sample suspected of comprising an antibody having specificity for a retrovirus selected from the group consisting of HIV-1 and HIV-2 with at least one peptide of the invention, a conjugate thereof coupled with a carrier, or a mixture thereof; and detecting any peptide-antibody or conjugate-antibody complexes formed.

Still part of the invention is a kit for the in vitro diagnosis of infection by a retrovirus selected from the group consisting of the HIV-1 and HIV-2 viruses, comprising in separate containers a composition comprising at least one of the peptides of the invention, a conjugate thereof with a carrier, or a mixture thereof;

at least one first reagent for the preparation of a medium suitable for carrying out an immunological reaction with the composition;

at least one further reagent for the detection of antigen-antibody complexes formed during an immunological reaction, the further reagent being selected from the group consisting of unlabeled and labeled further reagent; and at least one reference sample comprising a known quantity of antibodies capable of specifically binding to the composition that is free of any other antibodies.

Other subjects, advantages, and features of the present invention will become apparent to those skilled in the art from the following discussion.

BEST MODE FOR CARRYING OUT THE INVENTION

The present invention relates to new peptides corresponding to the gp41 envelope glycoprotein of HIV-1. These peptides can in particular be used in man for the in vitro diagnosis of an infection by the HIV-1 virus and they allow a high level of discrimination between infections caused by the HIV-2 viruses and those caused by the HIV-1 viruses.

Another aim of the present invention is to provide antigenic peptides whose amino acid sequence is modified so as to prevent the formation of undesirable disulphide bridges.

To designate hereinafter the amino acid residues which make up the peptides according to the invention, recourse will be had to the IUPAC-IUB standards which appear in Nucleic Acids Research 13, 3021–3030 (1985) and in the Biochemical Journal, 219, No. 2, 345–373 (1984).

The peptides of the invention which correspond to the envelope glycoprotein of HIV-1 have the following formula:

(Seq. ID NO: 1)    (1)
X—Arg—Ile—Leu—Ala—Val—Glu—Arg—Tyr—Leu—Lys—
Asp—Gln—Gln—Leu—Leu—Gly—Ile—Trp—Gly—Cys—Ser—
Gly—Lys—Leu—Ile—Cys—Z, in which X represents an NH group which is free or converted into an amide by one or two alkyl groups comprising from 1 to 5 carbon atoms, and Z represents either an OH group which is free or present as an alkoxy and thereby containing an alkyl group comprising from 1 to 5 carbon atoms, and are characterised in that at least one of the Cys residues is deleted, substituted or protected.

The present invention also relates to new peptides corresponding to the gp42 envelope glycoprotein of HIV-2. These peptides can be used especially for the in vitro diagnosis in man of an infection by the HIV-2 virus and allow a high level of discrimination between infections caused by the HIV-2 viruses and those caused by the HIV-1 viruses.

As in the case of the peptides derived from gp41 of HIV-1, another aim of the present invention is to provide antigenic peptides whose amino acid sequence is modified so as to prevent the formation of undesirable disulphide bridges.

This aim is achieved by virtue of the peptides of the invention which correspond to the HIV-2 envelope glycoprotein and have the following formula:

(Seq. ID NO: 2)    (II)
X—Ala—Ile—Glu—Lys—Tyr—Leu—Gln—Asp—Gln—Ala—
Arg—Leu—Asn—Ser—Trp—Gly—Cys—Ala—Phe—Arg—Gln—
Val—Cys—Z in which X represents an $NH_2$ group which is free or converted into an amide of one or two alkyl groups comprising from 1 to 5 carbon atoms, and Z represents either an OH group which is free or present as an alkoxy and thereby containing an alkyl group comprising from 1 to 5 carbon atoms, and in which at least one of the Cys residues is deleted, substituted or protected.

The deletion, the substitution or the protection of at least one of the Cys residues makes it possible to avoid the formation of disulphide bridges, and therefore the cyclisation or the polymerisation of the peptides. It was necessary in the case of the prior art peptides to use reducing agents in order to eliminate the disulphide bridges and thus avoid the detection of false positives during the use of these peptides in diagnostic processes.

The following are preferred by way of substitution or protection of at least one of the Cys residues.

The substitution of at least one of the Cys residues by a Ser residue.

The substitution of at least one of the Cys residues by an Ala residue.

The substitution of at least one of the Cys residues by a gamma aminobutyric acid residue.

The protection of at least one of the Cys residues by an acetamidomethyl group.

The substitution of the two Cys residues by an Asp residue and a Glu residue linked by an amide bridge.

The substitution of a Cys residue by a Ser residue, an Ala residue or a gamma aminobutyric acid residue, and the protection of a Cys residue by an acetamidomethyl group can, of course, be combined in the peptides of the invention.

The peptides according to the invention can be prepared using the conventional techniques of peptide synthesis in a solid phase, by successive condensation of amino acid residues in the required order, by condensation of amino acid residues on a previously formed fragment already containing several amino acids in the appropriate order or alternatively by condensation of several previously prepared fragments. These synthetic methods are conducted being careful initially to protect all the reactive functions carried by the amino acid residues or the fragments, with the exception of the amine and carboxyl functions engaged in the peptide bond formed during the condensation.

According to one example of preparation of the peptide of formula (I), the first amino acid residue whose amine function protected by a tert-butyloxy-carbonyl group attached to a resin through its carboxyl group, then after removing the protection of the amine function by washing the resin with trifluoroacetic acid in dichloromethane, the second amino acid residue Ile, whose amine function is protected as previously described, is coupled in the presence of dimethylformamide; the amino acid residues are thus attached one after the other. After removal of protection, the amine function of the N-terminal Arg residue can for example be acetylated by the action of excess acetic anhydride in the presence of diisopropylethylamine.

The side chains of trifunctional amino acids must protected especially by the following groups: cyclohexyl for glutamic acid, benzyl for threonine, tosyl for arginine, para-methylbenzyl for cysteine, 2,6-dichlorobenzyl for tyrosine, fluorenyl-methyloxycarbonyl or 2-chlorobenzyloxycarbonyl for lysine.

After removing all the protecting groups, the peptide according to the invention is released from the solid support. The crude product is freeze-dried and purified by moderate pressure liquid chromatography, which yields peptides of about 70% purity. The products are then purified by high pressure liquid chromatography, which yields peptides of 95% purity.

The invention also relates to the peptides modified by insertion and/or deletion and/or substitution of one or more amino acids, as long as the antigenic or immunogenic properties of the said peptides are not modified, as well as those in which the peptide bond (—CO—NH—) is replaced for exampled by the following structures:

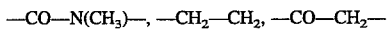

or alternatively in which the peptide backbone has one or more groups introduced such as —CH$_2$—, —NH— or —O— groups. The present invention furthermore encompasses peptides in which the amino acid residues presenting an asymmetric carbon are of the D or L form.

The invention furthermore relates to oligomers of monomers consisting of the peptides of the invention as well as an antigenic composition containing at least one of the said peptides, or at least an oligomer of this peptide specifically recognising the presence of anti-HIV-1 and/or anti-HIV-2 antibodies.

The oligomerisation can be carried out by any peptide polymerisation technique, the polymerisation being performed until an oligomer is obtained which contains the number of monomers which allow the desired immunogenicity to be obtained.

The invention furthermore relates to conjugates obtained by coupling of the peptides of the invention with carrier molecules, as well as the immunogenic composition containing at least one of the said peptides or at least an oligomer of this peptide or this peptide coupled with a carrier molecule, in association with a pharmaceutically acceptable vehicle, for the preparation of vaccines which induce the production of antibodies against the said peptides in sufficient quantity effectively to inhibit the HIV-1 and/or the HIV-2 retroviruses.

By way of example of carrier molecules, natural proteins such as tetanus toxoid, ovalbumin or serum albumins can be mentioned.

The peptides of the invention possess antigenic properties and can therefore be used in processes for the detection of an infection by the HIV-1 and/or HIV-2 viruses.

The invention therefore furthermore relates to a process for the in vitro diagnosis of infection by the HIV-1 and/or HIV-2 viruses, in a biological sample such as human serum generally comprising:

contacting a biological sample with at least one of the peptides according to the invention or a conjugate of this peptide with a carrier molecule; and detecting the possible presence of antigen-antibody complexes.

The detection of the antigen-antibody complexes which may be formed is advantageously carried out using immunoenzymatic, immunofluorescent, radioimmunological or radioimmunoprecipitation assays.

The invention therefore also relates to the above peptides labelled especially with a radioactive isotope, an enzyme, a fluorescent compound, an electrically charged molecule, a coloured particle, biotin, or an organometallic compound.

By way of an example of processes for the detection of anti-HIV-1 and/or anti-HIV-2 antibodies mentioned above, an indirect immunoenzymatic assay on human serum or plasma comprising the following steps can be mentioned in particular:

deposition of a defined quantity of a peptide of the invention, a mixture of peptide of the invention or a composition containing the said peptides into the wells of a microtitre plate;

distribution of a diluted serum or plasma under study, as well as positive and negative control sera in the said wells;

incubation for a sufficient period to allow attachment of the serum antibodies which may be present to the peptides of the invention specific for HIV-1 and/or to the peptides of the invention specific for HIV-2;

washing of the microplate;

introduction into the wells of a human anti-IgG conjugate labelled with peroxidase, which binds to the blood immunoglobulins attached to the solid phase;

elimination of the unbound fraction;

revealing the enzyme which may be present using a chromogenic substrate; and detection and comparison with the control sera.

The detection, the substitution or the protection of at least one Cys residue in the peptide of the invention prevents, during the deposition in liquid phase of the peptide of the microtitre plates, the formation of disulphide bridges and therefore the formation of polymer.

Among the processes for the detection of anti-HIV-1 and/or anti-HIV-2 antibodies according to the invention, is a rapid indirect immunoenzymatic serological assay comprising the following steps can furthermore be mentioned:

deposition of a defined quantity of at least one peptide of the invention on a membrane, which is saturated and then dried;

filtration through this membrane of a test serum (or plasma or whole blood); followed by the deposition of a conjugate (for example human anti-IgG coupled with peroxidase);

after washing, the reaction is developed by deposition of a chromogenic substrate of peroxidase. Only the anti-HIV-1 and/or anti-HIV-2 antibodies attached to the peptides are revealed in this reaction by a coloured signal, and a validating internal standard is included in the assay;

the presence of a coloured signal at the position of the preliminary deposition of the peptide as well as the presence of the validating internal standard allow positive interpretation (presence of anti-HIV-1 and/or anti-HIV-2 antibodies) for the test sample within a period of three minutes.

The invention finally relates to the reagents or kits for the in vitro diagnosis of infection by the HIV-1 arid/or the HIV-2 viruses, in a biological sample comprising:

a given quantity of at least one peptide according to the invention, a mixture of these peptides, or a conjugate of this peptide with a carrier molecule;

at least one reagent for the constitution of a medium suitable for carrying out an immunological reaction;

one or more reagents, which may be labelled, for the detection of antigen-antibody complexes formed during the immunological reaction;

at least one control sample free of antibodies or containing a known quantity of antibodies recognised by the said peptides.

In the case of a simultaneous detection of an infection by the HIV-1 and HIV2 viruses, two peptides can advantageously be used, each one specific for one of the viruses, labelled using different methods in order to be able to detect the presence of anti-HIV-1 and anti-HIV-2 antibodies.

Having now generally described this invention, the same will be better understood by reference to certain specific examples which are included herein for purposes of illustration only and are not intended to be limiting of the invention or any other any embodiment thereof, unless so specified.

EXAMPLES

A comparative study was carried out in order to show that the modifications performed on the Cys residues of the peptides of formula (I) and (II) do not affect their antigenic functionality.

EXAMPLE 1

Studies of Peptides Derived from the Envelope Glycoprotein of HIV-1 Virus

This study consisted of testing on sera of known reactivity, on the one hand, the native peptide of formula:

(Seq. ID NO: 1) (I)
Arg—Ile—Leu—Ala—Val—Glu—Arg—Tyr—Leu—Lys—Asp—
Gln—Gln—Leu—Leu—Gly—Ile—Trp—Gly—Cys—Ser—Gly—
Lys—Leu—Ile—Cys— and on the other hand, this peptide whose two Cys residues have been substituted by two Ser residues.

Each of the two peptides has been used in a serological diagnostic assay on a microtitre plate, according to the same procedure as follows.

EXAMPLE 2

Coating of microtitre plates

The peptides are dissolved in a liquid medium. After dilution with buffer to a concentration of 3 µg/ml, the wells of the microplates are coated using 100 µl of this solution for 16 hours at 37° C.

The plates are then emptied and 300 µl of saturating solution are added, 2 hours' incubation at laboratory temperature. After four washing cycles, the plates are dried at 37° C. before use (storage in air-tight bags containing a desiocating agent).

EXAMPLE 3

Reaction procedure

After prewashing the coated microtitre plate, 100 µl of the sample (serum of known reactivity diluted to 1/25) are deposited per well. Experimental controls are included in each series; incubatin is carried out for 15 minutes at room temperature.

After a second wash (4 cyles), to eliminate unbound serum antibodies, 100 µl of human anti-IgG antibody coupled with peroxidase (polyclonal antibody of goat origin) are distributed; incubation is carried out for 15 minutes at room temperature.

A final washing cycle is then carried out, and the peroxidase conjugate is revealed by 50 µl of OPD (ortho-phenylenediamine) substrate in the presence of $H_2O_2$; this incubation carried out for 5 minutes in the dark.

After appearance of the coloration, the chromogenesis reaction is stopped with 100 µl HCl (1N). The optical density (OD) is then read at 492 nm.

EXAMPLE 4

Results

In this study, the antigenicity of the native peptide of formula (I) is compared with that of its serine-substituted form (2 Set residues in place of 2 Cys residues). The study covered the following 18 sera, tested in duplicate:

7 anti-HIV-1 sera (including 6 seroconversion);

8 negatives;

2 anti-HIV-2;

1 isolated anti-p24;

as well as the 3 experimental controls:negative controls, anti-HIV-1 and anti-HIV-2.

The results, expressed in OD, are presented in Table 1 below.

TABLE I

| SERUM NUMBER | SERUM REACTIVITY | SERINE - SUBSTITUTED PEPTIDE OD at 492 nm in duplicate | NATIVE PEPTIDE OF FORMULA (I) OD at 492 nm in duplicate |
| --- | --- | --- | --- |
| 1 | Anti-HIV-1 | 2.434–2.435 | 2.412–2.419 |
| 2 | Seroconversion HIV-1 | 1.235–1.213 | 0.585–0.599 |
| 3 | Seroconversion HIV-1 | 2.246–2.244 | 1.457–1.832 |
| 4 | Seroconversion HIV-1 | 1.888–1.969 | 1.122–0.851 |
| 5 | Seroconversion HIV-1 | 2.601–2.712 | 2.726–2.695 |
| 6 | Seroconversion HIV-1 | 1.023–1.022 | 1.520–1.520 |
| 7 | Seroconversion HIV-1 | 0.291–0.322 | 0.290–0.307 |
| 8 | Anti-HIV-2 | 0.825–0.800 | 0.421–0.487 |
| 9 | Anti-HIV-2 | 0.061–0.069 | 0.077–0.117 |
| 10 | Anti-P24 | 0.071–0.046 | 0.016–0.026 |
| 11 | Negative | 0.053–0.052 | 0.052–0.054 |
| 12 | Negative | 0.045–0.055 | 0.034–0.042 |
| 13 | Negative | 0.044–0.037 | 0.051–0.043 |
| 14 | Negative | 0.036–0.032 | 0.018–0.021 |
| 15 | Negative | 0.068–0.065 | 0.050–0.060 |
| 16 | Negative | 0.046–0.045 | 0.034–0.031 |
| 17 | Negative | 0.019–0.014 | 0.004–0.006 |
| 18 | Negative | 0.063–0.098 | 0.068–0.061 |
| Negative Control | Negative | 0.023–0.026 | 0.012–0.014 |

TABLE I-continued

| SERUM NUMBER | SERUM REACTIVITY | SERINE - SUBSTITUTED PEPTIDE OD at 492 nm in duplicate | NATIVE PEPTIDE OF FORMULA (I) OD at 492 nm in duplicate |
|---|---|---|---|
| Control HIV-1 | Anti-HIV-1 | 1.354–1.346 | 1.296–1.305 |
| Control HIV-2 | Anti-HIV-2 | 0.024–0.018 | 0.018–0.021 |

EXAMPLE 5

Studies of Peptides Derived from the Envelope Glycoprotein of HIV-2 Virus

As in the case of HIV-1 peptides, this study consisted of testing on sera of known reactivity the native peptide of formula:

(Seq. ID NO: 2)                  (II)
Ala—Ile—Glu—Lys—Tyr—Leu—Gln—Asp—Gln—Ala—Arg—
Leu—Asn—Ser—Trp—Gly—Cys—Ala—Phe—Arg—Gln—Val—
Cys— as well as this peptide whose two Cys residues have been substituted, on the one hand by two Ser residues and, on the other hand, attached by a disulphide bridge.

Each of the three peptides was used in a serological diagnostic assay on a microtitre plate, according to the same procedure as follows.

EXAMPLE 6

Coating of microtitre plates

The peptides are dissolved in liquid medium. After dilution in buffer to a concentration of 3 µg/ml, the microplate wells are coated using 100 µl of this solution for 16 hours at 37° C.

The plates are then emptied and 300 µl of saturing solution are added; 2 hours' incubation at laboratory temperature. After four washing cycles, the plates are dried at 37° C. before use (storage in air-tight bags with a desiccating agent).

EXAMPLE 7

Reaction procedure

After prewashing the coated microtitre plate, 100 µl of the sample (serum of know reactivity, diluted to 1/25) are deposited per well. Experimental controls are included in each series; incubation is carried out for 15 minutes at room temperature.

After a second wash (4 cycles), to eliminate unbound serum antibodies, 100 µl of human anti-IgG antibody coupled with peroxidase (polyclonal antibody of goat origin) are distributed; incubation is carried out for 15 minutes at room temperature.

A final washing cycle is then carried out, and the peroxidase conjugate is revealed using 50 µl of OPD (ortho-phenylenediamine) substrate in the presence of $H_2O_2$; this incubation carried out for 5 minutes in the dark.

After appearance of the coloration, the chromogenesis reaction is stopped using 100 µl of HCl (1N). The optical density (OD) is then read at 492 nm.

EXAMPLE 8

Results

In this study, the antigenicity of the native peptide of formula (II) is compared with that of its serine-substituted form (2 Set residues in place of 2 Cys residues) as well as with that of its cyclic form (2 Cys residues attached by a disulphide bridge). The study covered the following 13 sera tested in duplicate:

6 anti-HIV-2 sera;

3 negatives;

2 anti-HIV-1;

2 isolated anti-p24;

as well as 3 experimental controls: negative controls, anti-HIV-1 and anti-HIV-2.

The results, expressed in OD, are presented in table II below.

TABLE II

| SERUM NUMBER | SERUM REACTIVITY | NATIVE PEPTIDE OF FORMULA (II) OD at 492 nm in duplicate | CYCLIC PEPTIDE OD at 492 nm in duplicate | SERINE - SUBSTITUTED PEPTIDE OD at 492 nm in duplicate |
|---|---|---|---|---|
| 1 | Anti-HIV-2 | 2.672–2.682 | 2.691–2.717 | 2.681–2.691 |
| 2 | Anti-HIV-2 | 2.508–2.505 | 2.518–2.519 | 2.416–2.417 |
| 3 | Anti-HIV-2 | 2.399–2.372 | 2.383–2.399 | 2.328–2.313 |
| 4 | Anti-HIV-2 | 2.247–2.252 | 2.253–2.188 | 2.252–2.190 |

TABLE II-continued

| SERUM NUMBER | SERUM REACTIVITY | NATIVE PEPTIDE OF FORMULA (II) OD at 492 nm in duplicate | CYCLIC PEPTIDE OD at 492 nm in duplicate | SERINE - SUBSTITUTED PEPTIDE OD at 492 nm in duplicate |
|---|---|---|---|---|
| 5 | Anti-HIV-2 | 1.951–1.956 | 1.911–1.949 | 1.762–1.781 |
| 6 | Anti-HIV-2 | 1.916–1.957 | 1.857–1.887 | 1.869–1.867 |
| 7 | Negative | 0.051–0.109 | 0.054–0.062 | 0.059–0.057 |
| 8 | Negative | 0.076–0.068 | 0.060–0.065 | 0.073–0.074 |
| 9 | Negative | 0.042–0.042 | 0.041–0.043 | 0.040–0.043 |
| 10 | Anti-HIV-1 | 0.091–0.094 | 0.066–0.067 | 0.123–0.183 |
| 11 | Anti-HIV-1 | 0.148–0.143 | 0.092–0.089 | 0.066–0.125 |
| 12 | Anti-P24 | 0.076–0.063 | 0.053–0.55 | 0.063–0.055 |
| 13 | Anti-P24 | 0.064–0.073 | 0.061–0.069 | 0.056–0.051 |
| Negative Control | Negative | 0.042–0.041 | 0.036–0.045 | 0.028–0.021 |
| Control HIV 1 | Anti-HIV-1 | 0.016–0.016 | 0.021–0.049 | 0.003–0.004 |
| Control HIV-2 | Anti-HIV-2 | 2.072–2.073 | 2.039–2.039 | 1.976–1.920 |

The invention now being fully described, it will be apparent to one of ordinary skill in the art that many changes and modifications can be made thereto without departing from the scope of the invention as set forth herein.

The peptide of formula (II) made cyclic by a disulphide bridge was studied by way of comparison, but does not form part of the peptides of the invention of which at least one of the Cys residues is modified in order to prevent the formation of any disulphide bridge. Yet, the disulphide bridge of the cyclic peptide is a weak bond which can easily be broken by oxygenation and therefore lead to polymerisation which is harmful for the quality of the assays.

The modifications carried out on the cysteine residues of the native peptides of formulae (I) and (II) do not alter their antigenic functionality, as they do not lower the reactivity; a homologous reactivity is recorded with sometimes stronger signals for the serine-substituted form.

Furthermore, these modifications prevent the possible polymerisation of the peptide (autopolymerisation, random cyclisation by cysteines) and thus allow the possible mixing of the peptides of the invention with other peptides containing free —SH groups, such as cysteines. These modifications also increase the batch-to-batch uniformity of production of the peptides of the invention.

Having now generally described this invention, the same will be better understood by reference to certain specific examples which are included herein for purposes of illustration only and are not intended to be limiting of the invention or any other embodiment thereof, unless so specified.

We claim:

1. An L-amino acid peptide having a formula selected from the group consisting of X-Arg-Ile-Leu-Ala-Val-Glu-Arg-Tyr-Leu-Lys-Asp-Gln-Gln-Leu-Leu-Gly-Ile-Trp-Gly-Cys-Ser-Gly-Leu-Ile-Cys-Z (SEQ ID No. 1) (I); and X-Ala-Ile-Glu-Lys-Tyr-Leu-Gln-Asp-Gln-Ala-Arg-Leu-Asn-Ser-TrP-Gly-Cys-Ala-Phe-Arg-Gln-Val-Cys-Z (SEQ ID No. 2) (II), wherein X represents $NR_2$, where R is hydrogen or ($C_1$–$C_5$) alkyl;

Z represents OR, wherein R is hydrogen or ($C_1$–$C_5$) alkyl; and at least one of the Cys residues is substituted with Ser; and combinations thereof.

2. The peptide of claim 1, wherein X is amino.

3. The peptide of claim 1, wherein Z is hydroxyl.

4. The peptide of claim 1 having the formula

X-Arg-Ile-Leu-Ala-Val-Glu-Arg-Tyr-Leu-Lys-Asp-Gln-Gln-Leu-Leu-Gly-Ile-Trp-Gly-Cys-Ser-Gly-Lys-Leu-Ile-Cys-Z (SEQ ID No:1) (I), wherein X is amino and Z is hydroxyl.

5. The peptide of claim 1, having the formula X-Ala-Ile-Glu-Lys-Tyr-Leu-Gln-Asp-Gln-Ala-Arg-Leu-Asn-Ser-Trp-Gly-Cys-Ala-Phe-Arg-Gln-Val-Cys-Z (SEG. ID. No: 2) (II), wherein X is amino, and Z comprises hydroxyl.

6. A polypeptide conjugate, comprising the peptide of claim 1 being linked to a carrier.

7. An antigenic composition, comprising at least one peptide of claim 1 or mixtures thereof.

8. The antigenic composition of claim 7, wherein the peptide specifically binds to an anti-retroviral antibody selected from the group consisting of anti-HIV-1 and anti-HIV-2 antibodies.

9. An antigenic composition, comprising the polypeptide conjugate of claim 6; and a pharmaceutically-acceptable vehicle.

10. An in vitro method of detecting antibodies selectively binding to a retrovirus selected from the group consisting of HIV-1 and HIV-2 in a biological sample, comprising contacting a biological sample suspected of comprising an antibody having specificity for a retrovirus selected from the group consisting of HIV-1 and HIV-2 with at least one peptide of claim 1, a conjugate thereof with a carrier, or a mixture thereof; and detecting any peptide-antibody or conjugate-antibody complexes formed.

11. The in vitro method of claim 10, wherein the detection of the peptide-antibody or conjugate-antibody complexes formed is carried out with an immunoenzymatic, immuno-fluorescence, radioimmunological or radioimmunoprecipitation assay.

12. A kit for the in vitro detection of antibodies selectively binding to a retrovirus selected from the group consisting of the HIV-1 and HIV-2 viruses, comprising in separate containers a composition comprising at least one peptide of claim 1, a conjugate thereof with a carrier, or a mixture thereof;

at least one first reagent for the preparation of a medium suitable for carrying out an immunological reaction with the composition;

at least one further reagent for the detection of antigen-antibody complexes formed during an immunological reaction; and at least one reference sample comprising a known quantity of antibodies capable of specifically binding to the composition but free of any other antibodies.

* * * * *

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 26 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:1:

```
Arg  Ile  Leu  Ala  Val  Glu  Arg  Tyr  Leu  Lys  Asp  Gln  Gln  Leu  Leu  Gly
 1                 5                          10                         15

Ile  Trp  Gly  Cys  Ser  Gly  Lys  Leu  Ile  Cys
                 20                         25
```

( 2 ) INFORMATION FOR SEQ ID NO:2:

( i ) SEQUENCE CHARACTERISTICS:
　　　　( A ) LENGTH: 23 amino acids
　　　　( B ) TYPE: amino acid
　　　　( D ) TOPOLOGY: unknown ( i i ) MOLECULE TYPE: peptide ( x i ) SEQUENCE DESCRIPTION: SEQ ID NO:2:

Ala Ile Glu Lys Tyr Leu Gln Asp Gln Ala Arg Leu Asn Ser Trp Gly
1               5                   10                  15

Cys Ala Phe Arg Gln Val Cys
            20